US008092219B2

(12) United States Patent
Neumeyer

(10) Patent No.: US 8,092,219 B2
(45) Date of Patent: Jan. 10, 2012

(54) TOOTH IMPLANT

(76) Inventor: Stefan Neumeyer, Eschlkam (DE)

( * ) Notice: Subject to any disclaimer, the term of this patent is extended or adjusted under 35 U.S.C. 154(b) by 897 days.

(21) Appl. No.: 11/795,955

(22) PCT Filed: Feb. 7, 2006

(86) PCT No.: PCT/DE2006/000203
§ 371 (c)(1),
(2), (4) Date: May 27, 2008

(87) PCT Pub. No.: WO2006/081815
PCT Pub. Date: Aug. 10, 2006

(65) Prior Publication Data
US 2011/0129797 A1   Jun. 2, 2011

(30) Foreign Application Priority Data
Feb. 7, 2005   (DE) .................. 10 2005 005 746

(51) Int. Cl.
*A61C 8/00* (2006.01)
(52) U.S. Cl. ........................................... 433/173
(58) Field of Classification Search .......... 433/172, 433/173, 174, 175, 176
See application file for complete search history.

(56) References Cited

U.S. PATENT DOCUMENTS

| 4,468,200 | A | | 8/1984 | Muench et al. |
| 4,596,574 | A | * | 6/1986 | Urist ............................. 424/422 |
| 5,989,026 | A | | 11/1999 | Rogers et al. |
| 6,461,160 | B1 | * | 10/2002 | Sutter ........................... 433/173 |
| 6,726,480 | B1 | | 4/2004 | Sutter |

FOREIGN PATENT DOCUMENTS

| DE | 10315399 | 9/2004 |
| EP | 1110514 | 6/2001 |
| WO | WO 0149199 | 7/2001 |
| WO | WO 2004/073541 A3 | 9/2004 |

* cited by examiner

*Primary Examiner* — Cris L Rodriguez
*Assistant Examiner* — Mirayda A Aponte
(74) *Attorney, Agent, or Firm* — Welsh Flaxman & Gitler LLC

(57) ABSTRACT

A tooth implant which has an implant body, which is, preferably embodied as a single piece with a support which is anchored in the bone tissue, in addition to a journal which is secured to one end of the implant body which is used to secure a constructional component. The journal has several groove-like recesses which are oriented, respectively, in the longitudinal direction thereof and, are distributed on the periphery of the journal and projections are arranged therebetween.

29 Claims, 13 Drawing Sheets

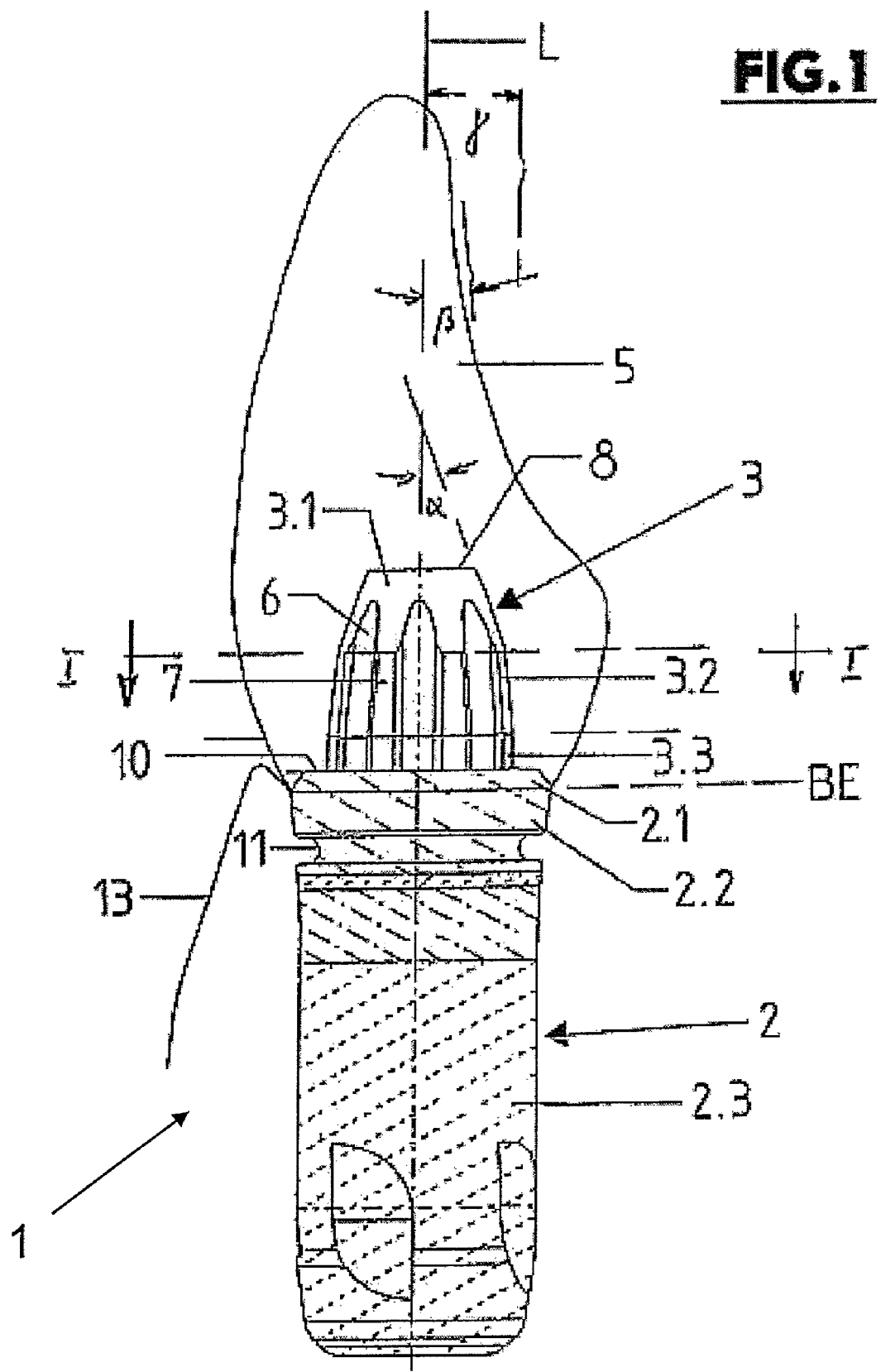

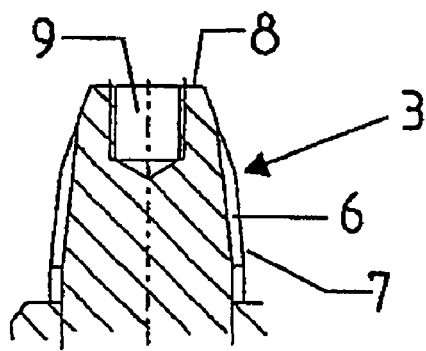
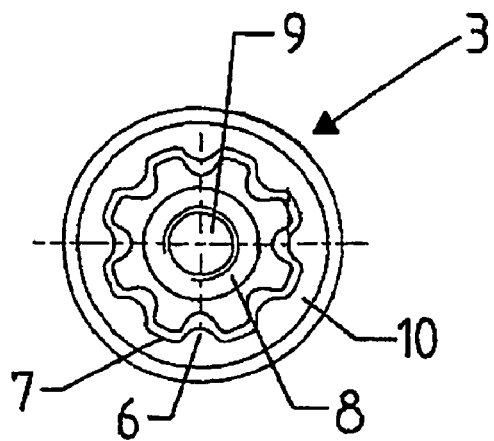
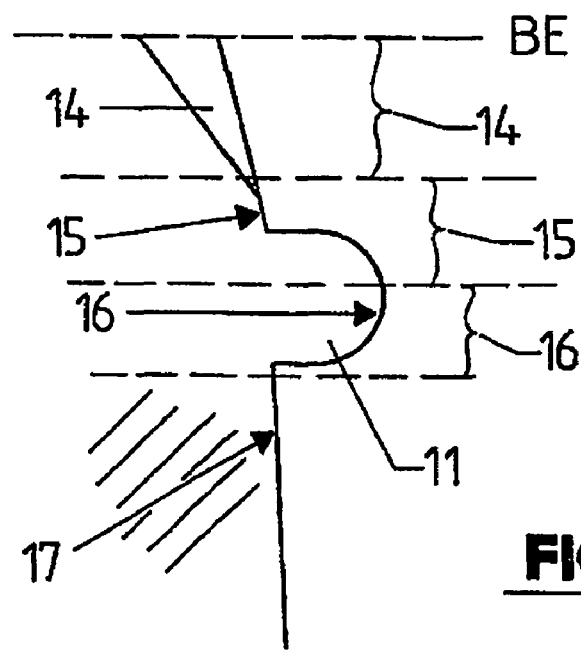

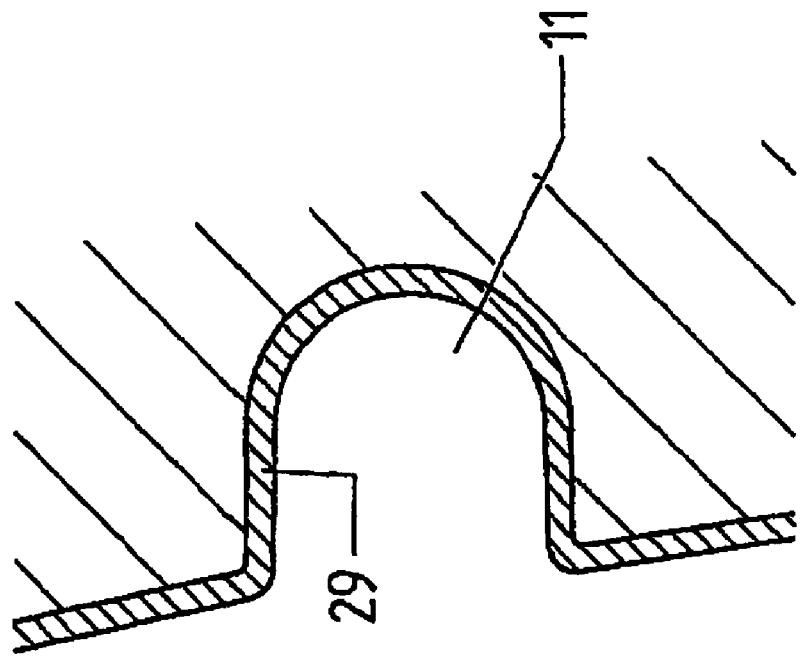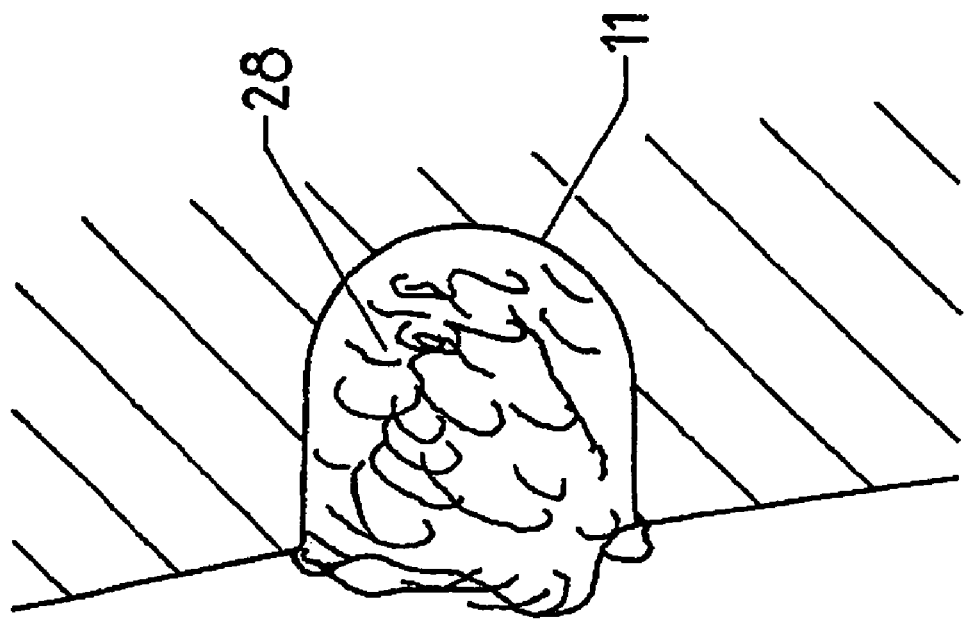

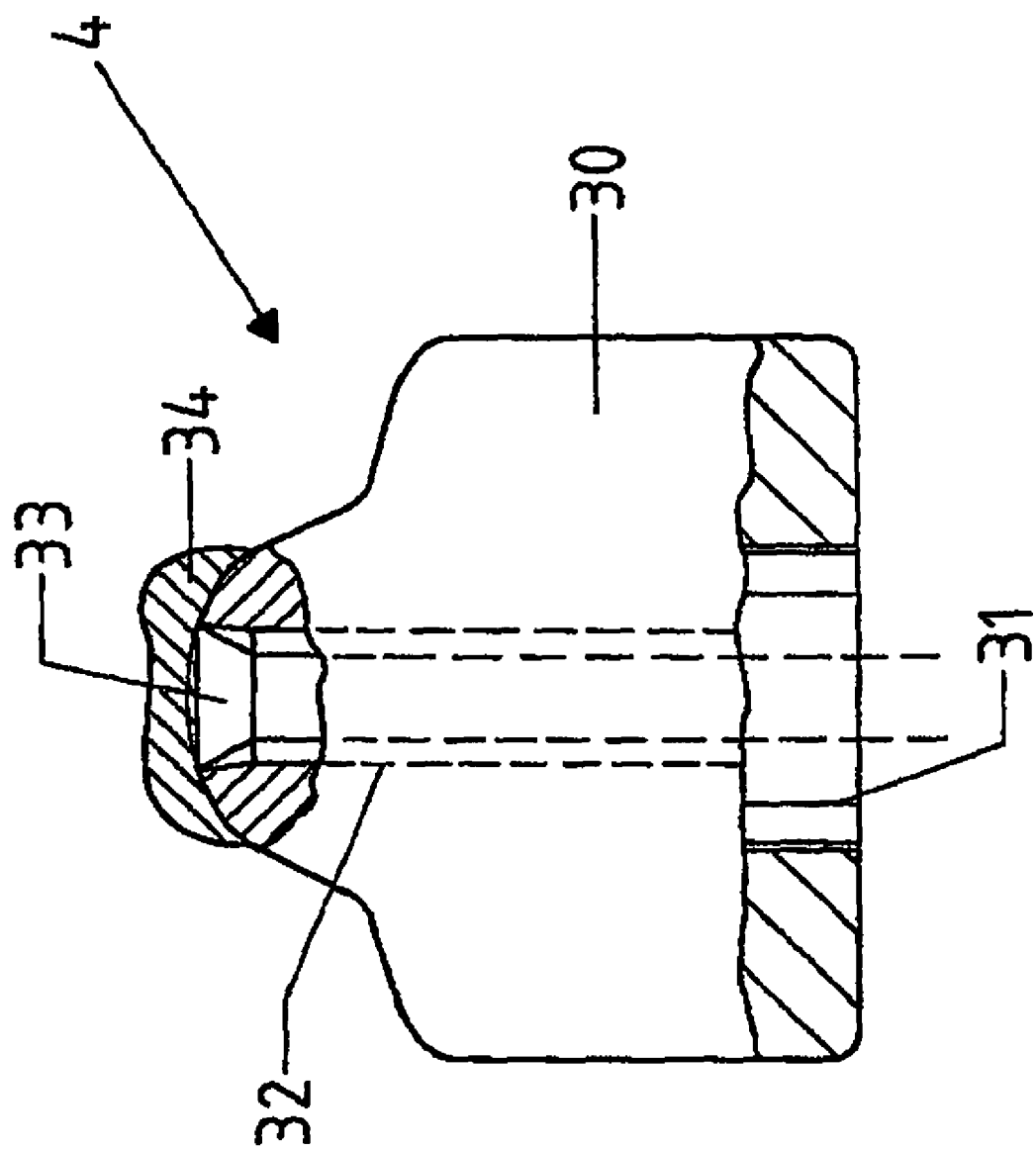

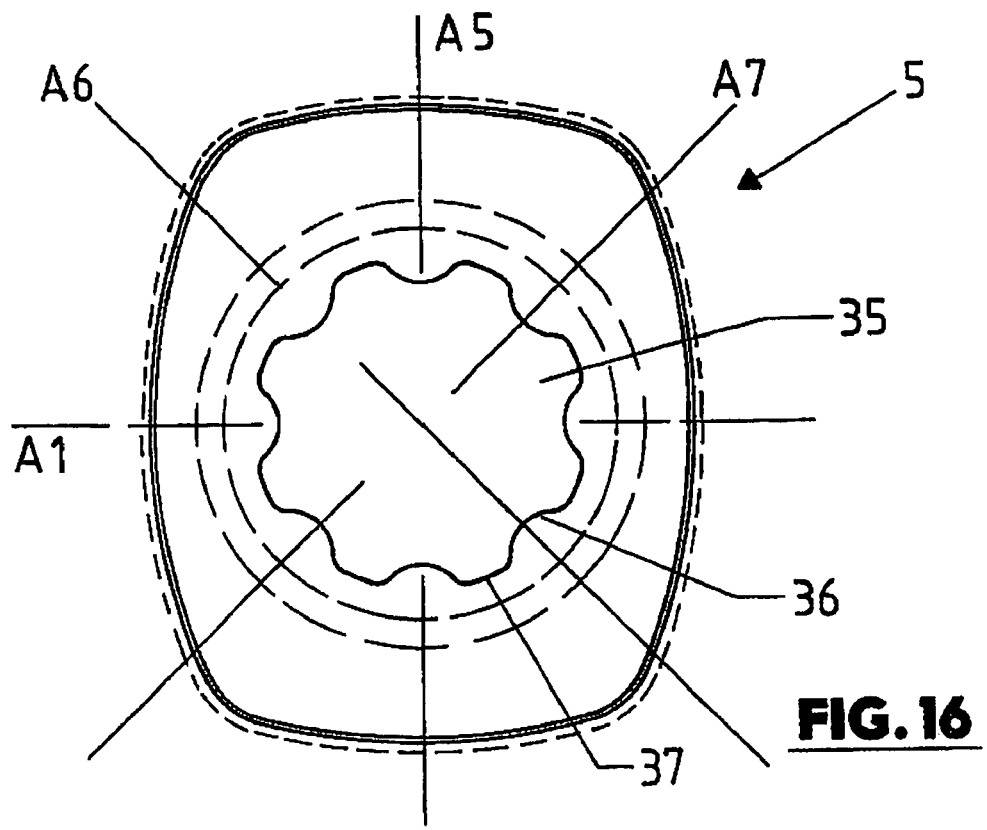
FIG. 16
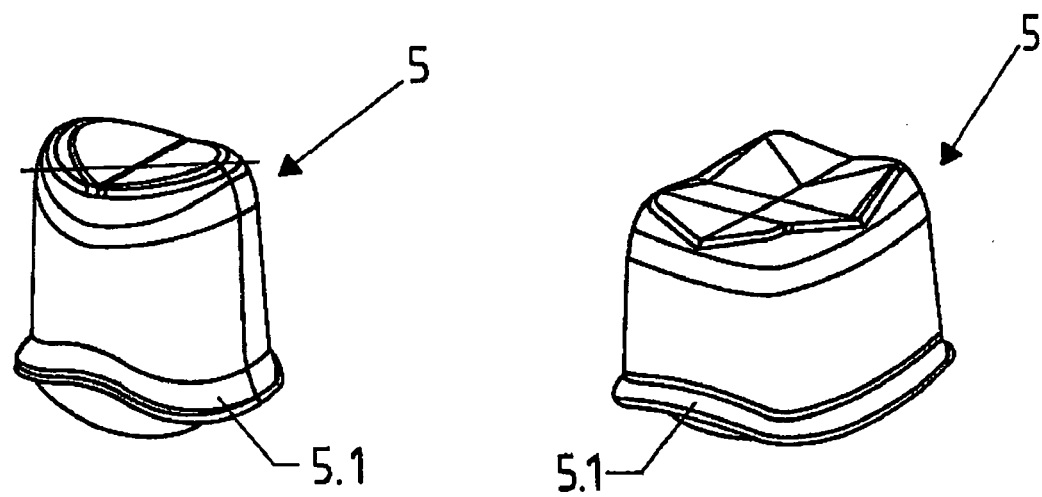
FIG. 17  FIG. 18

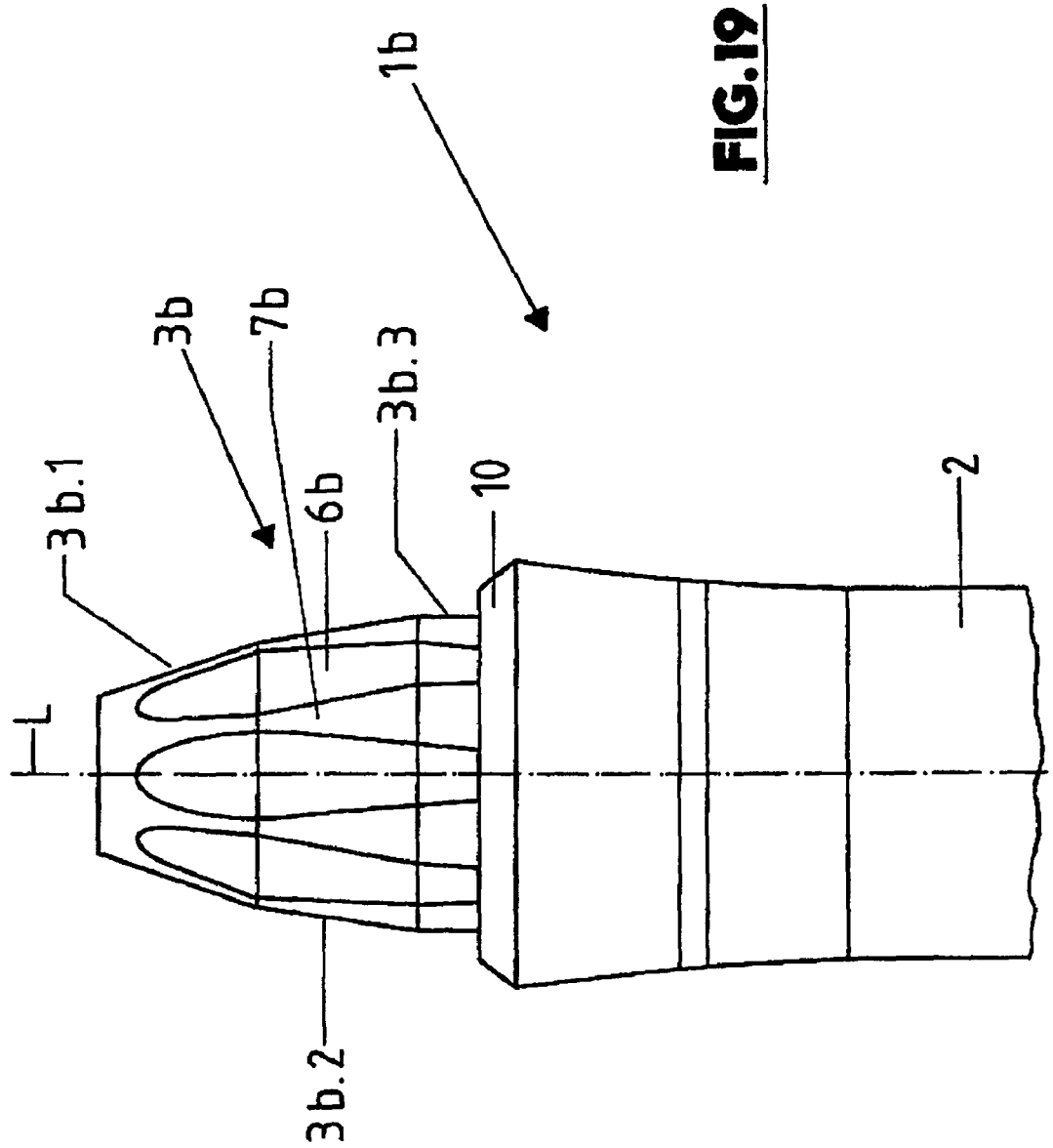

TOOTH IMPLANT

BACKGROUND OF THE INVENTION

The invention relates to a tooth implant manufactured as one piece with a post anchored in the bone tissue and with a journal on one end of the implant body for attaching a constructional component.

Many different types of tooth implants are known in the art.

It is an object of the invention is to present a tooth implant that is improved with respect to its utilization and also integration in the bone tissue.

SUMMARY OF THE INVENTION

The invention relates to a tooth implant which is made up of an implant body with a support which is anchored in the bone tissue, and a journal which is secured to one end of the implant body which is used to secure a constructional component. The journal has several groove-like recesses which are oriented in the longitudinal direction thereof and are distributed on the periphery of the journal, with projections therebetween.

BRIEF DESCRIPTION OF THE DRAWINGS

The invention is described below in more detail based on exemplary embodiments with reference to the drawings, in which:

FIG. 1 shows a simplified side view of a tooth implant according to the invention;

FIG. 2 shows a partial view in cross section of the journal of the implant of FIG. 1;

FIG. 3 shows the tooth implant of FIG. 1 in plan view from above;

FIG. 4 shows an enlarged view of the transition or gap between the implant and a cap attached to said implant, together with the adjoining tissue for illustration of the so-called "biological width";

FIG. 11 shows an enlarge view a recess area of the implant with a material inserted in to the recess.

FIG. 12 shows an enlarged view area of the recess of the implant having a coating on the recess;

FIG. 13 shows a simplified side view of a healing cap;

FIG. 16 shows a cross section corresponding to the line I-I of an alternate embodiment of a cap adapted to the natural shape of the tooth;

FIG. 17 show a perspective view of a cap formed as a premolar/molar;

FIG. 18 shows a perspective view of a alternate embodiment of a cap formed as a premolar/molar;

FIG. 19 shows in a view similar to FIG. 1 a further embodiment of the tooth implant according to the invention;

FIG. 20 shows a plan view of an alternate embodiment implant according to;

DETAILED DESCRIPTION OF THE INVENTION

Figure 5:
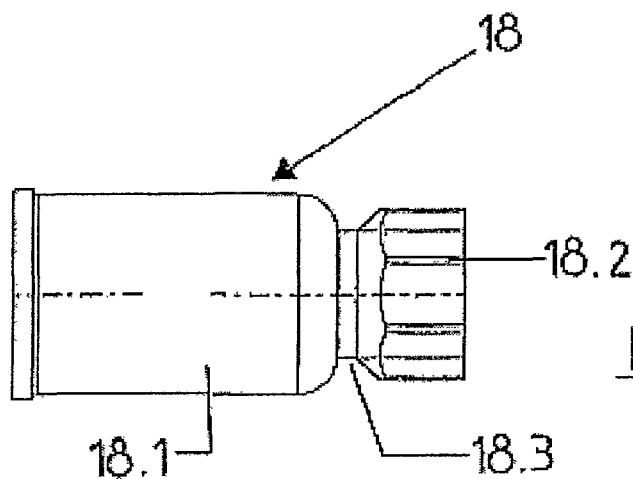
FIG. 5 show a side view of a screw-in adapter for use in the implant of FIG. 1.
Figure 6:
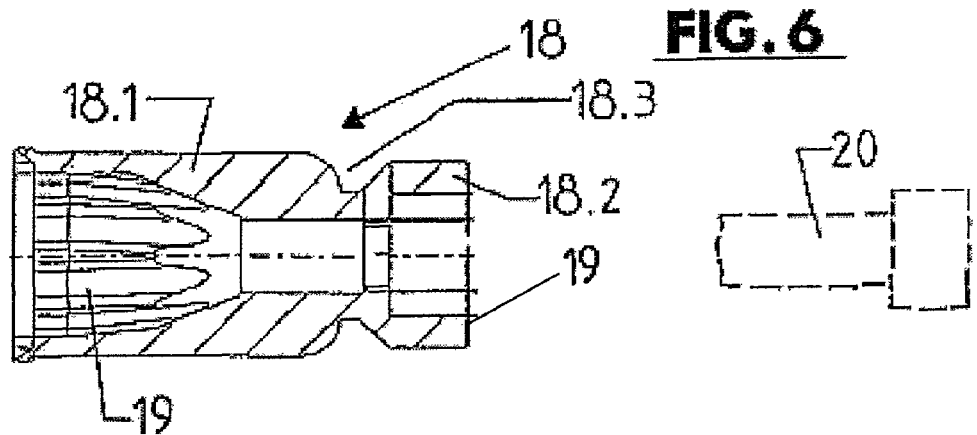
FIG. 6 shows a cross sectional side view of a screw-in adapter for use in the implant of FIG. 1;. with a cylindrical peripheral surface or peripheral contour.

The tooth implant generally designated 1 in FIGS. 1-3 is made as one piece from a suitable material, for example titanium, with a post 2 to be anchored in the jaw or in the bone tissue by screwing it in and with a journal 3 provided on an end of said post. The journal 3, which after setting the implant is used to secure a healing cap 4 (FIG. 13) and after healing of the implant is used to attach a cap 5 forming the restored or replaced tooth or another constructional component, is embodied as a so-called "Torx journal" in the present embodiment, with a total of eight groove-shaped recesses 6 on the periphery of the journal, which are oriented with their longitudinal extension in the direction of the longitudinal axis L of the implant 1. The recesses 6 have a concave rounded bottom and are also rounded at their transition into the projections 7 formed between the recesses 6.

The journal 3 forms at its upper free end at a distance from the post 2 a face surface 8, which in the depicted embodiment is flat and lies in a plane perpendicular to the longitudinal axis L of the implant and on which, in the depicted embodiment, a threaded hole 9 is provided on the same axis as the longitudinal axis L of the implant. Generally it is also possible to design the face surface 8 so that it is curved, for example concave or convex.

Starting from the face surface 8, the journal 3 comprises three sections with respect to its shape, namely a first journal section 3.1 that expands in a conical manner, the outer surface of which forms a first angle $\alpha$ with the longitudinal axis L of the implant, a second journal section 3.2, the outer surface of which forms a second angle $\beta$ with the longitudinal axis L of the implant, where the angle $\beta$ is smaller than the angle $\alpha$, and a third journal section 3.3, the outer surface or peripheral surface of which forms a third angle $\gamma$ with the longitudinal axis L of the implant that is smaller than the angle $\beta$. The above angles are, for example:

| Section | | |
|---|---|---|
| Journal section 3.1 | Journal section 3.2 | Journal section |
| $\alpha$<br>12-85° | $\beta$<br>4-12° | $\gamma$<br>0-3° |

In a preferred embodiment the angle $\alpha$ is 21°, the angle $\beta$ is 6° and the angle $\gamma$ is approximately 0°. On the section 3.3 in this embodiment, therefore, the outer surface of the journal 3 or the peripheral contour formed by the outer surface of the projections 7 is essentially cylindrical, although the axial length of the section 3.3 is much smaller than the axial length of the section 3.2, but also smaller than the axial length of the section 3.1.

The sections 3.1 and 3.2 or their outer contour formed by the outer surfaces of the projections 7 is therefore conical or essentially conical. The outer surface of the journal 3 in the area of the journal section 3.2 or the outer contour of said journal formed by the outer surface of the projections 7 is slightly conical or cylindrical in the area of the section 3.3. The notches formed between the projections 7 correspond for example to the three-stage form of the outer contour of the journal 3. The three-stage form of the journal achieves an optimum transfer of the forces from the constructional component attached solely by adhesion to the journal 3 and the restored or replaced tooth or crown (cap 5), so that when subjected to a load, especially in the constructional component at the transition to the journal 3, no load peaks will occur that could destroy or damage the constructional component.

As further depicted in FIG. 1, the projections 7 and the recesses or notches formed between said projections extend to the ring surface 10 enclosing the journal 3.

FIG. 3 is a plan view of the journal 3, depicting that the projections 7 in the area of the transition between the sections 3.1 and 3.2 in the plan view 3 have a relatively distinct trapezoidal cross section with only slightly rounded corners. Generally, it is also possible, however, to form the projections 7 and the groove-shaped recesses 6 formed between said projections so that a wave-shaped, sinus course is created for the projections 7 and the recesses 6 between them in the view of FIG. 3, and that the projections 7 are rounded so that the outer contour of the projections as depicted in FIG. 3 corresponds to the contour of the recesses 6.

Especially the angles α and β are selected so that for the cap or the constructional component placed on the journal 3, the largest possible material thickness in the area surrounding the journal is achieved, i.e. the angles α and β are selected so that the peripheral or outer surface of the sections 3.1 and 3.2 extend parallel to the outer surface of the cap 5 or the constructional component adjoining said sections or form an angle with said outer surface, which opens toward the side of the cap 5 facing away from the posts 2, so that a sufficient material thickness and therefore a sufficient stability for the cap in the area surrounding the journal 3 is ensured, namely for each form of the cap 5 or of the constructional component, i.e. both as a front tooth or incisor and as a premolar/molar.

The journal section 3.1 is adjoined in the direction of the post 2 by a journal section 3.2, on which the outer surface of the journal 3 or the peripheral contour of the journal 3 formed by the outer surface of the projections 7 is likewise conical, however with a much smaller conical angle from the section 3.1, for example with a conical angle of 6° from the longitudinal axis L of the implant.

The section 3.2 is then finally adjoined by a section 3.3, on which the outer surface of the journal 3 or the peripheral contour formed by the outer surfaces of the projections 7 is essentially cylindrical, although the axial length of the section 3.3 is much smaller than the axial length of the section 3.2, but also smaller than the axial length of the section 3.1.

The bottom of each recess 6 follows the contour of the outer surface of the journal 3, i.e. the journal section 3.2 has an angle on the longitudinal extension of each recess 6 with the longitudinal axis L of the implant that is equal to or approximately equal to the smaller conical angle of the journal section 3.2. On the journal section 3.3 the longitudinal extension of each recess 6 is oriented parallel to the longitudinal axis L of the implant.

The outer diameter of the journal 3 or of the journal section 3.3 at the transition to the post 2 is smaller than the outer diameter of the upper post section 2.1 shown in FIG. 1 adjoining the journal 3, resulting in a ring surface 10 at the transition between the journal 3 and the post 2, enclosing the journal 3 and lying in a perpendicular plane to the longitudinal axis L of the implant.

The post section 2.1 in the depicted embodiment is likewise conical, namely so that said post section increases in diameter toward the lower end of the tooth implant 1 located at a distance from the journal 3. The journal section 3.1 is adjoined by a further journal section 3.2, which is likewise conical, namely so that said post section 2.2, the axial length of which is greater than the axial length of the section 2.1, is slightly conical toward the end of the post 2 located at a distance from the journal 3. The post section 2.2 is adjoined by a post section 2.3, which is provided with outer threads and with which the tooth implant 1 is anchored in the bone tissue of the jaw by being turned in or screwed in.

In the area of the journal section 3.3 the tooth implant 1 is conical slightly conically in partial sections, for example at the top and bottom end of said post section. In between, the section 3.3 has an essentially cylindrical outer contour.

Between the two sections 2.2 and 2.3, a recess 11, in this embodiment ring-shaped and concentrically enclosing the longitudinal axis L of the implant and forming a so-called switched platform, is made in the post 2, by means of which a reduction or reformation of the bone tissue after healing of the implant is prevented permanently or over an extended period, as described in more detail below.

After healing of the implant, the constructional component (e.g. the cap 5) is attached to the journal 3, using a suitable adhesive or cement. For this purpose, the cap 5 has an opening that is adapted to the form and contour of the journal 3, which is further embodied so that it also overlaps the post section 2.1. The transition between the two post sections 2.1 and 2.2 therefore forms a gap or a reference plane BE for the so-called biological width, as will be described below.

The implant 1 is inserted for optical or cosmetic reasons in the manner that after attaching the cap 5 on the healed implant 1, said reference plane BE, in the view selected for FIG. 1, is below the top of the adjoining soft tissue designated 13 in FIG. 1, i.e. said transition is optically covered by the soft tissue 13 abutting the cap 5 and therefore this transition between the cap 5 and the implant 1, and in particular also the implant 1 itself, are not visible.

FIG. 4 shows the situation in the area of the transition between the cap 5 and the tooth implant 1 again in detail and in an enlarged view. According to the principle of "biological width" a so-called sulcus, designated 14 in FIG. 4, is formed in the area of the reference plane BE, i.e. a pocket-like recess enclosing the healed implant 1, namely with a depth of approximately 0.5 to 0.7 mm starting from the reference plane BE or the transition between the implant and the cap 5 on the outer surface. Adjoining the sulcus 14, a so-called epithelial attachment develops with the implant 1, which, starting from the sulcus 14, extends a distance of approximately 1.0 to 1.2 mm along the implant. Following this, the connective tissue attachment 16 develops, namely in the manner that the distance along the implant from the reference plane BE to the bone tissue 17 is approximately 2.5 to 3.00 mm.

These lengths are defined biologically. Since for optical reasons the transition between the implant and the constructional component in the implant 1 is relatively deep in the soft tissue 13, the development of the so-called sulcus is also displaced into the soft tissue or in the direction of the bone tissue 17, so that due to the principle of "biological width", after healing of the implant, the bone in the area of the implant will re-form over the course of time, unless suitable preventive measures are taken.

To prevent the bone from re-forming, the invention provides for a recess 11 at the transition between the post sections 2.2 and 2.3. The implant 1 is then set so that essentially only the post section 2.3 is held in the bone tissue 17, while the sulcus 14, the epithelial attachment 15 and the connective tissue attachment 16 develop on the post section 2.2 and in the area of the recess 11. The invention is based on the knowledge that not the distances measured in the axis direction parallel to the longitudinal axis L of the implant are decisive for the "biological width", but rather the distances along the outer surface of the implant 1. The recess 11 increases this distance so that despite the deeper transition between the constructional component or cap 5 and the implant, the distances defined by the principle of "biological width" are maintained, thus preventing re-formation of the bone tissue 17.

The recess 11 according to the invention is referred to as a switched platform.

A screw-in adapter 18 used for setting or screwing in the implant 1 is made of a high-strength material, for example steel, titanium or another suitable metal alloy, in the depicted embodiment namely with a section 18.1 of the adapter 18 that is essentially cylindrical on the outer surface and which is adjoined by a section 18.2 embodied as a hexagon. Between two sections 18.1 and 18.2, a ringed groove 18.3 is provided, through which the two sections are optically separated from each other. Furthermore, the adapter 18 has a bore hole 19 that is on the same axis as the axis of the adapter and is adapted to the shape of the journal 3 in the area of the section 18.1, so that the adapter 18 can be placed on the journal 3 for screwing in the implant 1 positively and tightly. A screw 20 extending through the bore hole 19 and engaging in the threaded hole 9 secures the adapter 18 on the implant 1 or on the journal 3 during setting or insertion of the implant 1.

After screwing in the implant, the screw 20 is loosened so that the adapter 18 can then be pulled out and re-used after being sterilized. The adapter 18 serves only as an orientation aid during insertion of the implant, i.e. the axial length of the adapter 18.1 corresponds to the height of a normal molar or premolar and the entire axial length of the adapter 18 corresponds approximately to the height of a front tooth. This then makes it possible to optimize the insertion depth of the implant 1, and the axial length of the sections 18.1 is clearly discernible by the groove 18.3 between the two sections 18.1 and 18.2, and said groove also improves visibility during setting of the implant.

Figure 7:
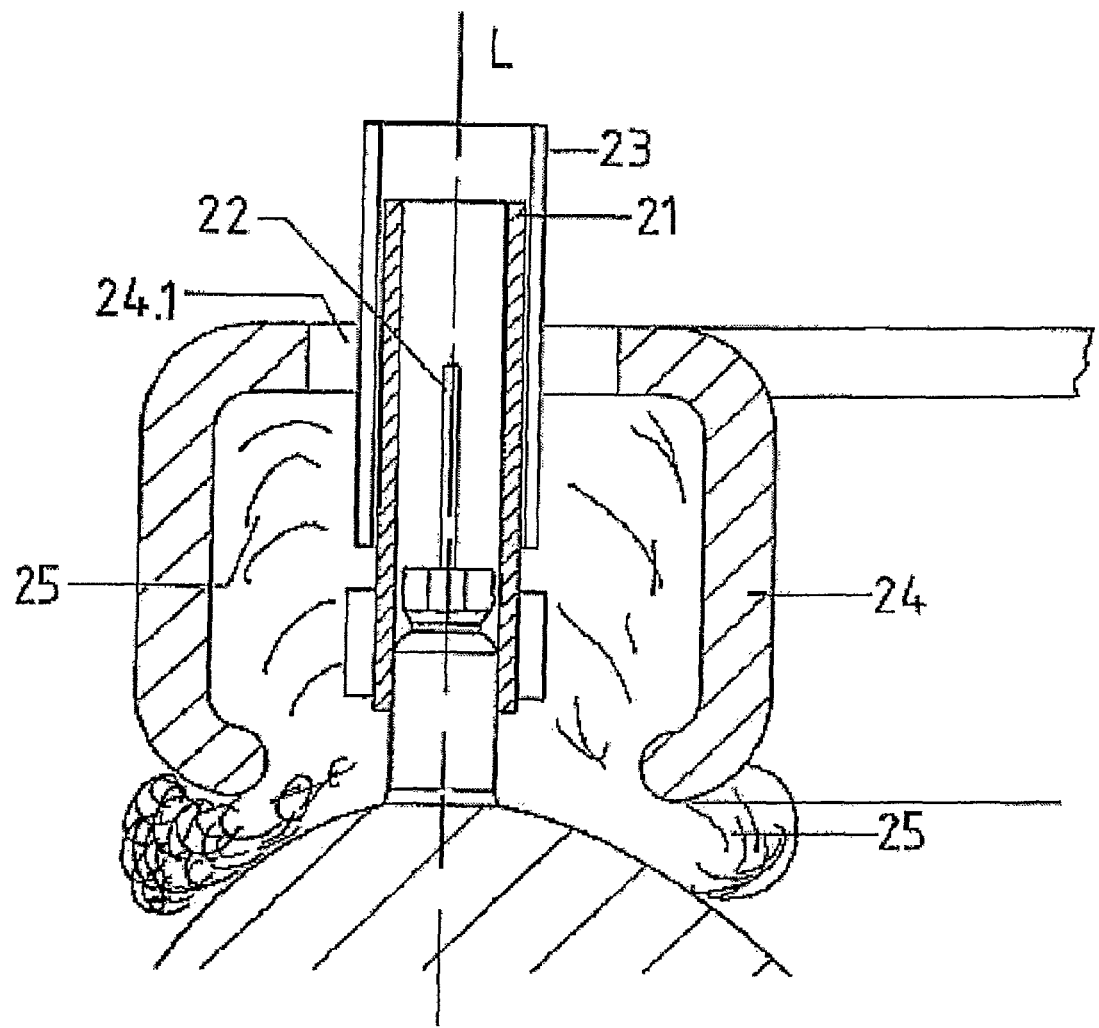
FIG. 7 shows a schematic view of a situation for preparing an impression with an impression spoon and an impression mass in a labial-lingual cross-section plane.

FIG. 7 shows in a simplified view the situation during preparation of an impression in the area of the implant that is set using the adapter 18. For the impression, a support sleeve 21 is pushed onto the adapter 18, which is connected by means of the screw 20 with the implant 1, and attached in a suitable manner to the adapter 18. For this purpose the sleeve 21 in the depicted embodiment is slotted (slot 22) at least in the area of its end to be pushed onto the adapter 18. An axially movable clamping sleeve 23 is provided on the sleeve 21 so that when the clamping sleeve is pushed in the direction of the end of the sleeve 21 holding the adapter, it clamps the sleeve 21 on the adapter. Both sleeves 21 and 22 are open on their ends that are distant from the adapter 18. The impression is prepared using a conventional impression spoon 24 and the usual impression mass 25. During this process, the two sleeves 21 and 23 are guided through an opening 24.1 provided in the impression spoon 24. The impression can likewise be used in the normal manner to manufacture the model of the upper or lower jaw, respectively, using the usual modeling mass, such as plaster.

To remove the impression, a suitable tool is used to release the screw 20, so that the adapter 18 together with the remaining impression can be removed and forms part of said impression, so that the journal 3 and the post section 2.1 adjoining said journal are reproduced in the model.

To prevent twisting of the sleeve 21 in the impression mass 25, the sleeve 21 is provided with radially projecting elements, for example with wing-shaped elements 21.1. Instead of or in addition to these, corresponding elements to prevent twisting can also be provided on the clamping sleeve 23.

It was assumed above that while preparing the impression the adapter 18 is held on the implant 1 by means of the screw 20. Other means are also conceivable. After creating the model, the sleeves 21 and 23, and in particular also the adapter 18, are removed from the impression mass 25, so that these elements can be re-used after being cleaned and sterilized.

Figure 8:
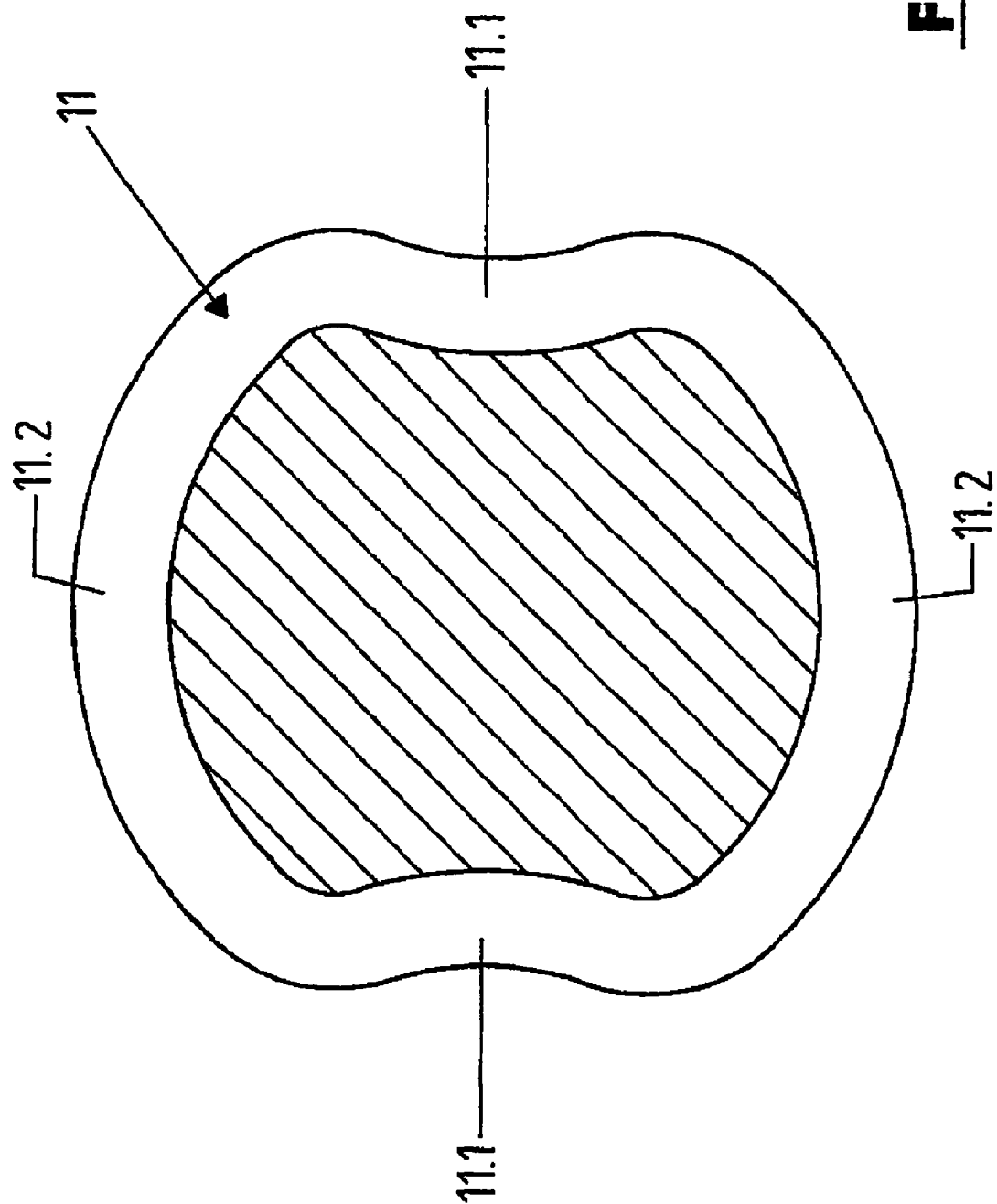
FIG. 8 shows a cross section of the tooth implant corresponding to the section line 1-1 of FIG. 1 in a further possible embodiment.

The natural anatomical structure of the upper or lower jaw bone in the vicinity of a tooth, however, is such that it generally has a greater height in the interdental area than in the labial and lingual area. In order to maintain this shape of the bone while allowing for the principle of "biological width", the hollow or recess 11 is embodied according to FIG. 8, so that it has a different depth, i.e. at two areas 11.1 offset by 180° from the longitudinal axis L of the implant, the recess 11 is deeper than at two areas 11.2 offset respectively by 90° from these areas 11.1. The implant is then set so that the areas 11.1 are located in the interdental area, so that, allowing for the distance resulting from the principle of "biological width" between the sulcus and the transition between the connective tissue and jaw, which (distance) is defined along the implant primarily by the deeper section 11.1, the greater height for the transition between connective tissue and bone tissue in the interdental area is maintained.

Figure 9:
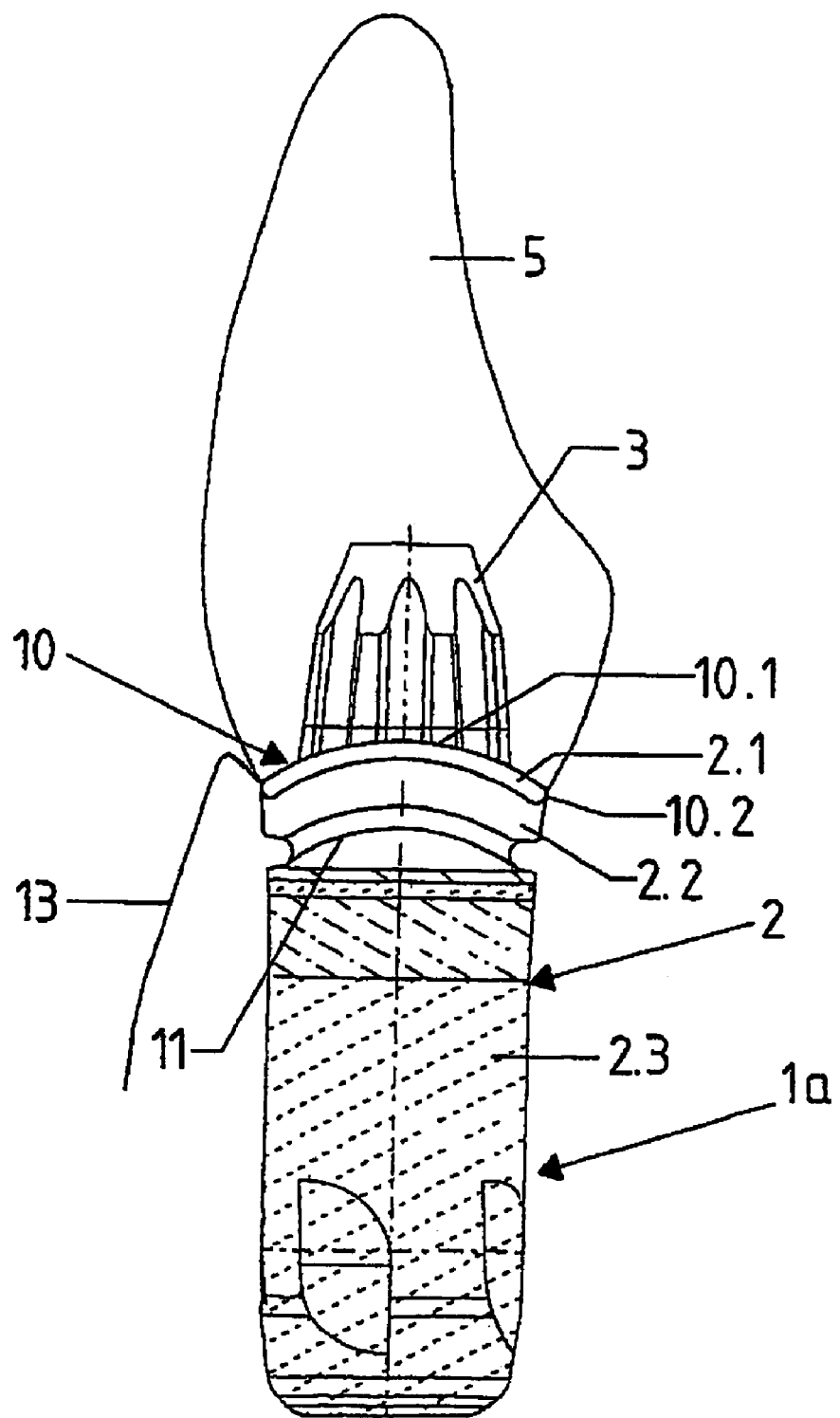
FIG. 9 shows in a view similar to FIG. 1 a further possible embodiment of the tooth implant according to the invention.

FIG. 9 shows in a view similar to FIG. 1 as a further embodiment a tooth implant 1a, which differs from the implant 1 essentially in that the journal section 2.1 is not flat on its top side facing the journal 3 and forming the ring surface 10, but rather garland-shaped in the manner that the ring surface 10, offset by 180° from the longitudinal axis L of the implant, forms two raised sections 10.1 with a somewhat greater distance from the lower end of the implant 1a in FIG. 9 and, in between those sections, two lower sections 10.2 with a smaller distance from the free end. The lower end of the respective constructional component, for example the cap 5, is then designed accordingly. Furthermore, the recess 11 follows said garland-shaped course. The implant 1a is set so that the sections 10.1 are located in the interdental area, thus achieving and maintaining the higher level of the transition between the connective tissue and bone tissue. Of course, the recess 11 provided for this implant can additionally be embodied with a different depth corresponding to FIG. 7.

Figure 10:
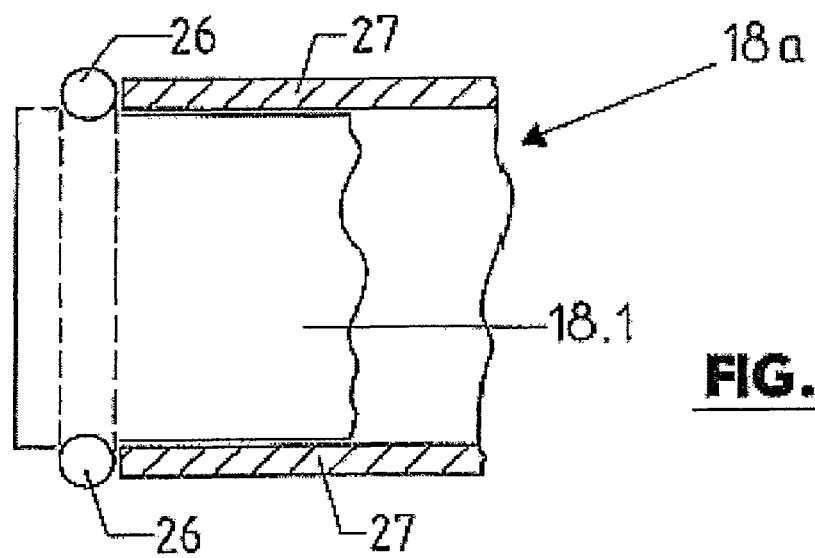
FIG. 10 shows a partial view of a further embodiment of the screw-in adapter.

FIG. 10 shows as a further possible embodiment an adapter 18a, which differs from the adapter 18 in that the free end of the adapter section 18.1 is provided with a ring groove, in which a ring 26 made for example of a rubber-elastic material is partially held. When attaching the constructional component, for example the cap 5, on the healed implant 1 or 1a, i.e. on the journal 3 there, first the adapter 18a is again placed on the journal 3 and secured there in a suitable manner, for example by means of the screw 20. Afterwards, using a suitable tool, for example a sleeve 27, the ring 26 is pushed from the adapter 18a onto the implant 1 or 1a, i.e. onto the section 2.2. The ring then forms a seal during cementing of the constructional component or cap 5 to prevent penetration of cement into the sulcus 14.

FIGS. 11 and 12 again show, in an enlarged view, the implant 1 or 1a in the area of the recess 11. As depicted, a material 28 that promotes the healing process can be inserted into said recess or a coating 29 made of such a material can be applied; this material or coating can also be a tissue material occurring naturally in the body.

To improve the integration of the implant 1 or 1a both in the soft tissue and connective tissue and also in the bone tissue, the post sections 2.1, 2.2 and 2.3, in addition to the recess 11, are structured in a particular manner on the surface, namely the section 2.3 both in the area of the threads and at the recesses between the threads. The structuring corresponds for example to the structuring found on a peach pit.

In particular, the surface structuring is embodied so that it has small but deep pores in the area of the post section 2.2 and in the area of the recess 11 and deep but coarse structures in the labial and lingual areas.

In the bone area, i.e. in the section 2.3, the structuring changes starting from the recess 11 toward the free end of the implant, namely in the manner that in an upper partial area adjoining the recess 11, the structuring formed by the deep pores has a course oriented in the direction of the longitudinal axis L of the implant, and in an adjoining partial or intermediate area the structuring formed by the pores is embodied or oriented to cover a large area with an increasing pore size moving downward in the direction of the longitudinal axis L of the implant and also in an axis direction that is perpendicular thereto, partially also curved or bulged, and in the lower area, i.e. at the lower, free end of the post section 2.3, the structuring formed by the pores is oriented essentially perpendicular to the longitudinal axis L of the implant.

FIG. 13 shows a simplified side view of a healing cap 4 for use with the implant 1 or 1a. The healing cap 4 is manufactured from a suitable plastic, for example, as a mushroom-shaped molded body (30). The cap 4 has an indentation 31, which is adapted to the shape of the journal 3, so that the cap with said indentation can be placed onto the journal 3 of the corresponding implant 1 or 1a, namely in the manner that the cap 4 rests full-surface with its bottom side on the conical surface of the section 2.1 and the lower, outer edge of the healing cap 4 or of the cap body 30 lies either flush with the outer edge of the post section 2.1 or with the transition between the sections 2.1 and 2.2, or is offset radially somewhat from said edge or transition, but in no case protrudes over the outer edger of the section 2.2. This achieves that the transition or gap from which the sulcus 14 develops during healing of the implant is displaced as far as possible to the upper or outer side of the tissue, thus preventing reduction of the bone during healing.

The cap body 30 is further provided with a through bore 32, so that the cap 4 can be secured on the implant 1 or 1a by means of a screw 33 engaging in the threaded bore 9. After insertion of the screw 33, a seal 34 is applied to the cap body 30 in order to tightly seal the cap 4 especially in the area of the screw 33. The material used for the cap body 30, for example plastic material, is a suitable sealing material for this purpose, for example a plastic that can be hardened with UV light to form the seal 34.

Preferably the healing cap 4 is further embodied so that it not only is adapted on its bottom side to the form of the implant 1 or 1a, but also the bottom side of the cap body corresponds in shape and size to the constructional component (cap 5) to be attached to the implant at a later time.

The respective constructional component or the respective cap 5 is provided with an indentation 35 adapted to the form of the journal 3, the peripheral surface of which, corresponding to the form of the journal 3, comprises a plurality of projections 36 and recesses 37 in between; the recesses 37 are arranged on a common, imaginary surface line, which corresponding to the form of the journal 3 likewise comprise the three sections with the different angles α, β and γ relative to the axis of the indentation 35. When the constructional element is mounted on the journal 3, each projection 36 is held by a notch in the journal 3 formed between two projections 7. Each projection 7 of the journal 3 engages in a matching recess 37.

In order to achieve optimum conditions with regard to distribution of forces when the journal 3, which is attached solely by gluing, is subjected to a load, the projections 36 are provided for reinforcement of the thickness of the constructional component and for increasing the load capacity at the same place where a natural tooth is subjected to the main loads. For all caps 5 or similar constructional components or crowns, this is primarily the axis direction defined by the connecting line between the two lateral surfaces or interdental surfaces of the cap 5 or of a natural tooth. In any case, a projection 36 is provided on each side of the axis of the indentation 35 in this axis direction designated A1 in FIGS. 14-16.

Figure 14:
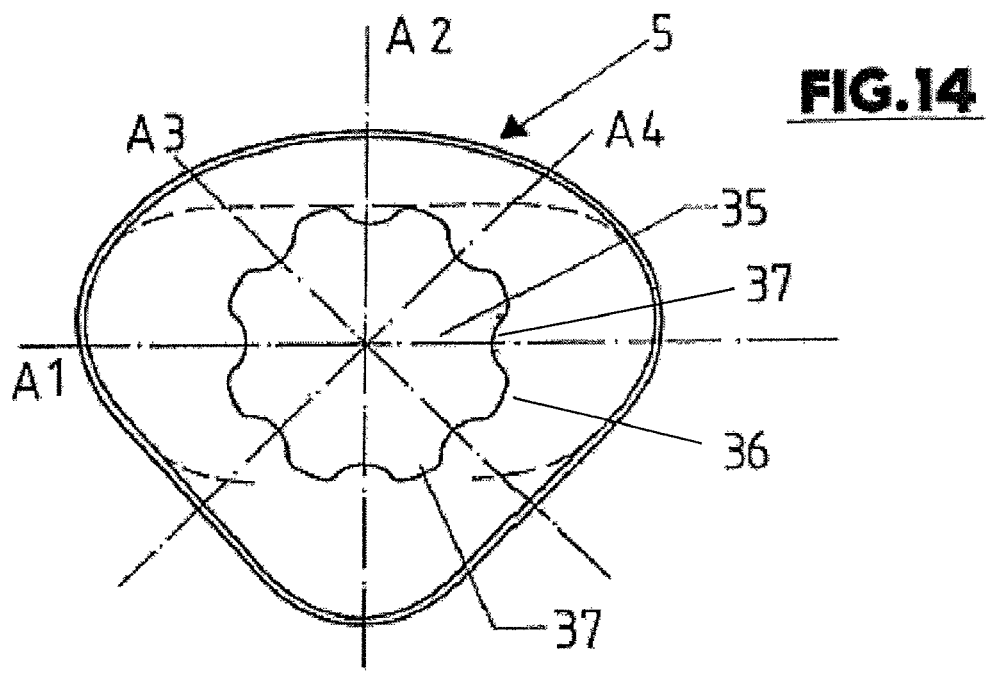
FIG. 14 show a cross section corresponding to the line 1-1 a cap adapted to the natural shape of the tooth.

In the constructional component 5 depicted in FIG. 14 in cross section and corresponding to an incisor, there are two further projections or bulges 36 on the connecting line A2 between the labial surface and the palatinal surface of the constructional component 5. Further projections 36 are provided in the cross section view of FIG. 14 between the axis directions A1 and A2 in the axes A3 and A4.

Figure 15:
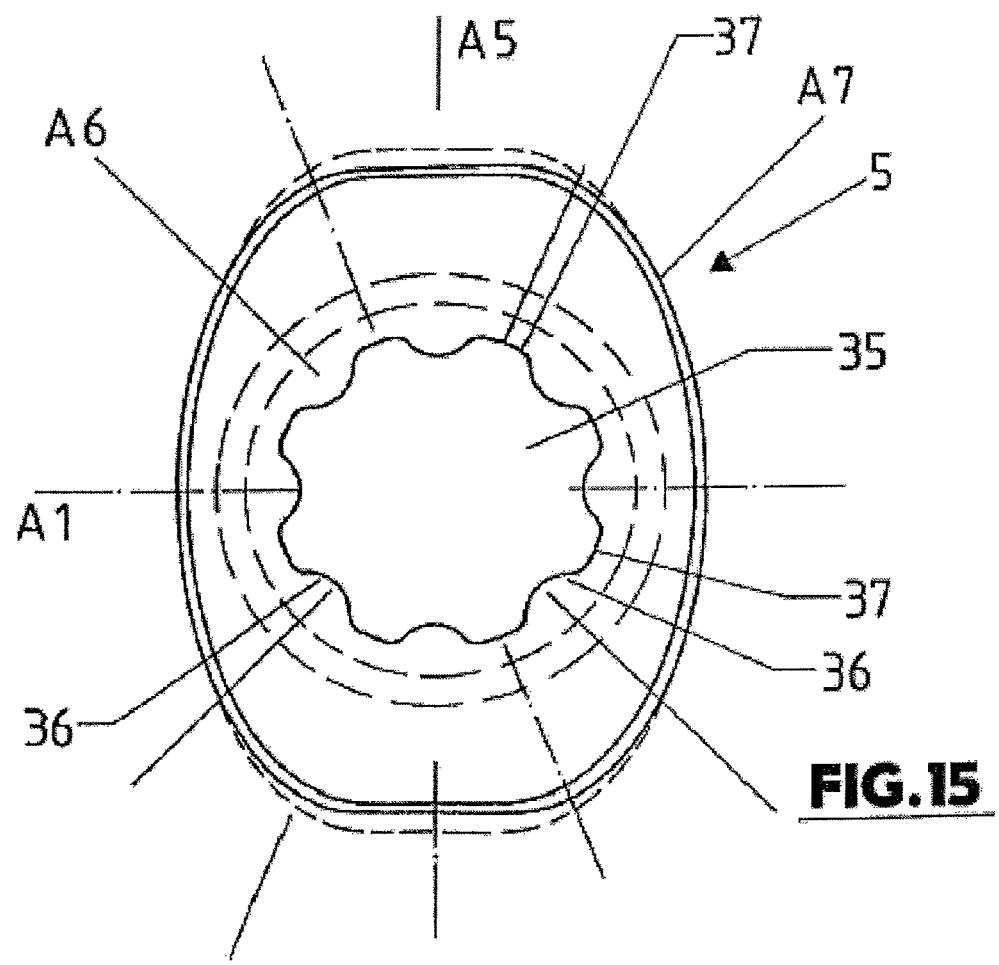
FIG. 15 shows a cross section corresponding to the line I-I of an alternate embodiment of a cap adapted to the natural shape of the tooth.

FIG. 15 shows a cross section of a cap 5 corresponding to a premolar. The indentation 35 is embodied here so that two further projections 36 oppose each other in an axis direction A5, which is defined by the connecting line between the palatinal and buccal surfaces of the constructional component 5. Further projections 36 oppose each other in the cross section view of FIG. 15 in axis directions A6 and A7, which extend between the axis directions A1 and A5 and respectively form an angle of 45° with these axis directions.

FIG. 16 shows a cross section of a cap 5 embodied as a molar. Here, the projections 36 of the indentation 35 are arranged in the same manner as described above in connection with FIG. 15 for the cap 5 or the corresponding constructional component embodied as a premolar.

Furthermore it is possible to design the journal 3 and/or the constructional components or caps 5, and also the healing caps 4, so that the respective cap is locked into place when it is placed on the journal 3. This makes it possible to secure the respective healing cap during the healing process and/or to keep the cap 5 or another constructional component in the specified, exact position, at least until the glue has hardened.

Furthermore, it is possible to structure the inner surface of the indentation 35, i.e. to provide it with a roughened surface or with small notches, etc. to improve the adhesive joint. Furthermore, it is possible to reinforce the respective constructional component or the cap 5 especially in such areas where increased loads occur, by means of fibers, for example also by means of nanofibers.

FIGS. 17 and 18 again show the cap 5 embodied as a premolar/molar in a perspective view. The caps 5 in this embodiment are provided on their bottom side comprising the opening 35 for the respective journal 3 with a slightly projecting cap edge 5.1, which has a garland-shaped course in the manner that the distance between the top side of the cap and the edge 5.1 is smallest in the area of the axis A1, i.e. in the interdental area.

FIG. 19 shows as a further possible embodiment an implant 1b, which differs from the implant 1 in the structuring of the journal 3. Although the journal 3 in this embodiment has the recesses 6b and the projections 7b corresponding to the recesses 6 and the projections 7, the recesses are formed so that starting from the ring surface adjoining the post 2, the width of the recesses first increases toward the free journal end and then decreases again, with the maximum width of the recesses 6b being at the point where the journal section 3b.1 corresponding to the journal section 3.1 makes the transition to the journal section 3.2 corresponding to the journal section 3b.2.

Corresponding to the recesses 6b, the projections 7b have a changing width, namely in the form that each projection 7b, starting from the ring surface 10 in the direction of the free journal end, first has a decreasing width and then an increasing width.

Figure 20:
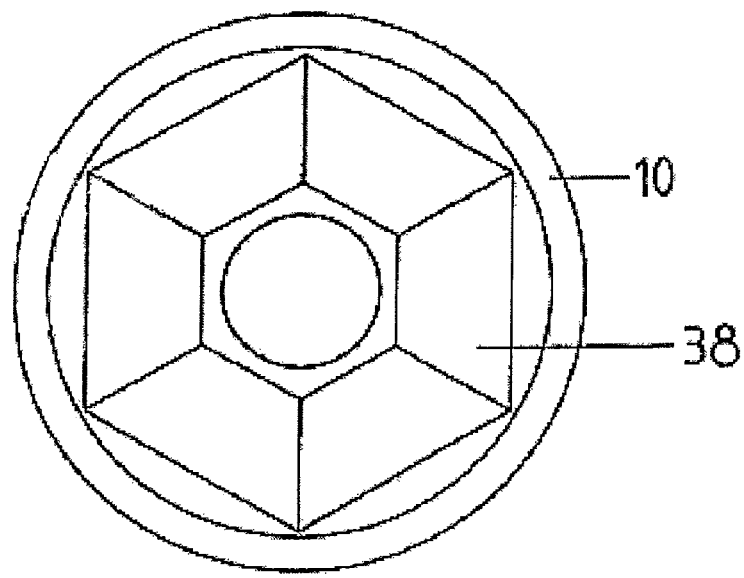
Figure 21:
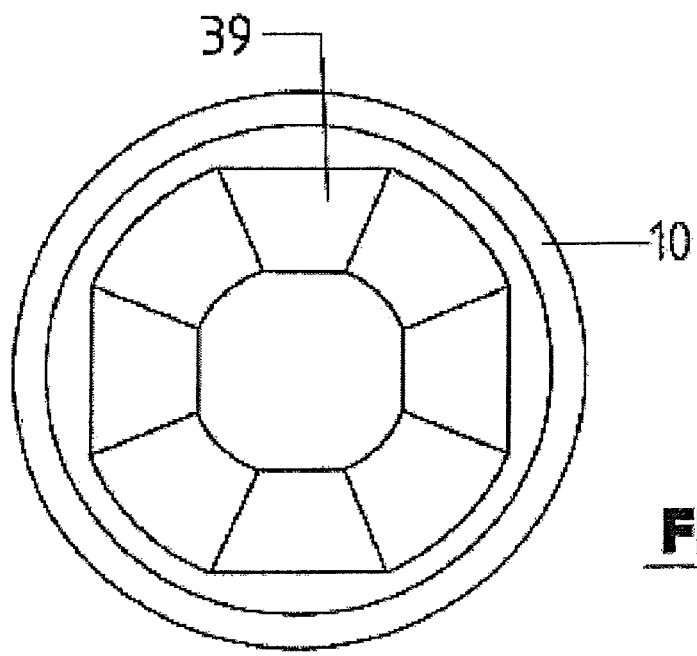
FIG. 21 shows a plan view of an alternate embodiment implant according to the invention.

It was assumed above that he journals 3 and 3b comprise recesses 6, 6b and projections 7, 7b, respectively. Generally, it is also possible to design the journals of the implant without such projections, namely with the three conical or cylindrical sections 3.1, 3.2 and 3.3. Furthermore, it is possible to design peripheral or outer surfaces of these sections in the form of flat, adjoining polygonal surfaces, as depicted in FIG. 20 for the journal 38, or as a combination of flat and curved surfaces, as depicted in FIG. 21 for the journal 39.

Furthermore, it is possible to design the respective journal so that said journal or at least one journal section forms an angle with the longitudinal axis of the implant, for example the angle α, which changes along the periphery.

Figure 22:
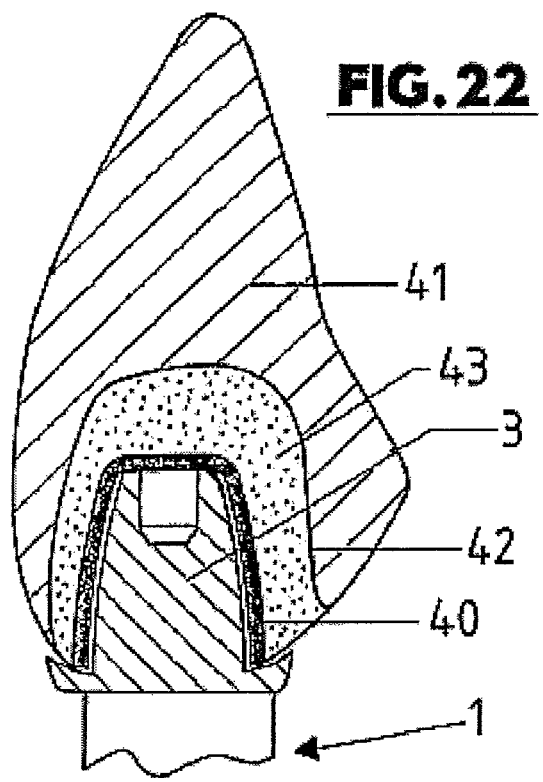
FIG. 22 shows a cross section of a natural tooth and the journal of an implant.

FIG. 22 again shows the journal 3, together with a sleeve 40 mounted on said journal, the sleeve having a small layer thickness, for example a layer thickness between 0.05 and 1.0 mm. The sleeve 40 exactly reproduces the contour of the journal 3. Reference number 41 designates a natural tooth, in which a hole is drilled on the bottom at 42. The tooth 41 is used as a cap in this embodiment. For this purpose, the sleeve 40 is inserted into the bore hole 42 and anchored with a suitable filling material 43, so that the natural tooth 41 can then be anchored as a constructional element on the implant or on the journal 3.

Figure 23:
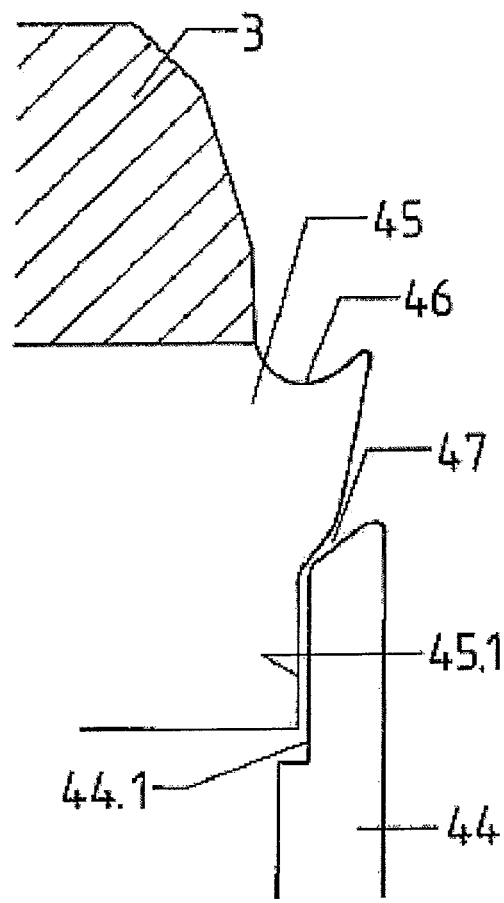
FIG. 23 shows a partial view of a two-part implant.

FIG. 23 shows a partial view of a two-part implant, which consists of the component 44 forming the post and the component 45 forming the journal 3. Instead of the ring surface 10, this implant or its component 45 comprises a circumferential hollow channel 46, which again has the garland-shaped course. This hollow channel serves for example to collect cement during joining of the implant and the constructional component. At the top edge of the component 44 between the two components, a gap 47 is formed, which functions as a switched platform, namely in the same manner as described above for the recess 11. This gap 47 or this switched platform also has the garland-shaped course.

The two components 44 and 45 are designed so that when the component 45 is inserted in the component 44 or in a recess 44.1 there with the section 45.1, a torsionally stable joint exists between the two components. For this purpose, the recess in the component 44 has a non-circular cross section, for example a hexagonal cross section. The section 45.1 is provided with a corresponding outer cross section. The recess 44.1 also serves as a tool gripping surface during setting of the implant or of the component 44.

Figure 24:
FIG. 24 shows a schematic view of a garland-shaped course of a switched platform.

FIG. 24 again shows schematically the garland-shaped course both of the hollow channel 46 and of the gap 47 or of the switched platform. The height h between the lower and the upper maximum of the garland-shaped course for an implant for a front tooth or incisor is between 1.2 and 2.5 mm, for an implant for a premolar between 0.9 and 1.5 mm and for an implant for a molar between 0.5 and 0.9 mm, depending on the course of the switched platform and the longitudinal axis of the implant. If the switched platform progresses corresponding to the form indicated in FIG. 8 on the longitudinal axis of the implant with concave sections 11.1, then the smaller value applies. If the switched platform progresses corresponding to FIG. 8 also convexly on the sections 11.1, then the higher values for h apply.

The invention was described above based on exemplary embodiments. It goes without saying that numerous modifications or variations are possible without abandoning the underlying inventive idea upon which the invention is based.

REFERENCE TERMS

1, 1a tooth implant
2 post
2.1, 2.2, 2.3 post section
3 journal
3.1, 3.2, 3.3 journal section
4 healing cap
5 constructional component or cap
6 recess
7 projection
8 face surface
9 threaded hole
10 ring surface
10.1, 10.2 sections of ring surface 10
11 recess
11.1, 11.2 sections of recess
13 soft tissue
14 sulcus
15 epithelial attachment
16 connective tissue attachment
17 bone
18, 18a adapter
18.1, 18.2 section of adapter 18
18.3 groove-shaped recess
19 bore hole
20 screw
21 sleeve
22 slot
23 clamping sleeve
24 impression spoon
24.1 opening in impression spoon 24
25 impression mass
26 ring
27 tool
28 material promoting the healing process
29 coating
30 cap body of healing cap 4
31 indentation
32 bore hole
33 screw
34 seal
35 indentation
36 projection
37 recess
38, 39 journal
A1-A7 axis direction
α, β, γ angle
L longitudinal axis of implant

The invention claimed is:

1. A tooth implant with an implant body, manufactured as one piece with a post anchorable in a bone tissue and comprising a journal on one end of the implant body for attaching a constructional component, wherein the journal is embodied with several groove-like recesses which are distributed on a periphery of said journal and, oriented longitudinally in a longitudinal direction (L) of the implant and projections arranged in between and wherein an outer surface of the journal comprises a conical first section, a conical second section and a third section with a cylindrical peripheral surface or peripheral contour which adjoin each other in the longitudinal direction (L) of the implant, and of which the first section located nearer a free end of the journal forms with its peripheral surface a first angle ($\alpha$) with the longitudinal axis (L) of the journal, the second section following the first section in a direction toward the post forms with its peripheral surface a second angle ($\beta$) with the longitudinal axis (L) of the journal, and the third section following the second section in the direction toward the post forms with its peripheral surface a third angle ($\gamma$) with the longitudinal axis (L) of the journal, where the third angle is smaller than the second angle and the second angle is smaller than the first angle.

2. The tooth implant according to claim 1, wherein the first angle ($\alpha$) is between approximately 12° and 85°, the second angle ($\beta$) is between approximately 4° and 12° and the third angle ($\gamma$) is between approximately 0° and 3°.

3. The tooth implant according to claim 1, wherein the first angle ($\alpha$) is approximately 21°, the second angle ($\beta$) is approximately 6° and the third angle ($\gamma$) is approximately 0°.

4. The tooth implant according to claim 1, wherein at least the first and second sections are conical.

5. The tooth implant according to claim 1, wherein the journal, starting from a journal end at a distance from the post comprises a first conical section with a larger conical angle, and adjoining said first section, a second conical section with a smaller conical angle, and adjoining said second section, a third section with a cylindrical peripheral surface or peripheral contour.

6. The tooth implant according to claim 1, wherein the groove-like recesses extend in the second and third section of the journal.

7. The tooth implant according to claim 1, wherein the journal end has a flat or essentially flat face surface.

8. The tooth implant according to claim 1, wherein the journal end is provided with a threaded bore hole on its free end.

9. The tooth implant according to claim 1, wherein eight groove-like recesses are distributed on the periphery of the journal.

10. The tooth implant according to claim 1, wherein a post section to be anchored in the bone tissue comprises at least one recess that at least partially encloses the longitudinal axis (L) of the implant for increasing a distance between a transition from the constructional component to the implant and the bone tissue, wherein the at least one recess is a ring-shaped groove enclosing the longitudinal axis (L) of the implant.

11. The tooth implant according to claim 10, wherein the at least one recess has a garland-shaped course.

12. The tooth implant according to claim 1, further comprising a ring surface enclosing the journal at a transition to the post and forming a shoulder or step.

13. The tooth implant according to claim 12, wherein the ring surface is arranged in a perpendicular plane to the longitudinal axis (L) of the implant.

14. The tooth implant according to claim 12, wherein the ring surface has a garland-shaped course.

15. The tooth implant according to claim 1, wherein the constructional component with a form corresponding to that of a natural tooth with an indentation adapted to the shape and size of the journal in order to suitably hold said journal, and the indentation comprises projections on its inner surface distributed around its axis and recesses in between, and that at least two projections oppose each other in an axis direction (A1) on both sides of a middle axis of the indentation, said axis direction being defined by the connecting line between the lateral surfaces or interdental areas of the constructional component.

16. The tooth implant according to claim 15, wherein when the constructional component is embodied as a front tooth or incisor, at least two further projections oppose each other on a middle axis of the indentation in a second axis direction (A2), which is defined by the connecting lines between a labial side and a palatinal side of the constructional component.

17. The tooth implant according claim 15, wherein when the constructional component is embodied as a premolar or a molar, at least two further projections oppose each other on the middle axis of the indentation in a third axis direction (A5), which is defined by the connecting lines between a palatinal side and a buccal side of the constructional component.

18. The tooth implant according to claim 15, wherein further projections are provided between the at least two projections.

19. claim 15, wherein each projection of the indentation engages in a recess of the journal and a projection of the journal engages in each recess of the indentation.

20. The tooth implant according to claim 1, further comprising a screw-in adapter placed on the journal and secured there by means of a screw.

21. The tooth implant according to claim 20, wherein the screw-in adapter comprises two adapter sections adjoining each other in a longitudinal direction of the adapter, of which one section can be placed tightly on the journal of the implant and the other section forms at least one tool gripping surface.

22. The tooth implant according to claim 21, wherein an axial length of the one adapter section is equal to or approximately equal to the height of a natural molar or premolar.

23. The tooth implant according to claim 20, wherein an entire axial length of the adapter is equal to or approximately equal to the height of an incisor.

24. The tooth implant according to claim 21, wherein the two adapter sections have different colors or are optically separated by a recess, or the two adapter sections have different colors and are optically separated by a recess.

25. The tooth implant according to claim 20, wherein a ring is provided on the screw in adapter that can be pushed onto the tooth implant when the adapter is connected with the tooth implant.

26. The tooth implant according to claim 1, further comprising a healing cap mounted on the journal and secured there by means of a screw.

27. The tooth implant according to claim 1, wherein the at least one recess serving to increase a distance between the transition from the constructional element to the implant and the bone tissue is provided with a material that promotes growing or healing or with a coating made of such a material.

28. The tooth implant according to claim 1, further comprising a healing cap, wherein a top side of a healing cap facing the tooth implant corresponds in size or shape to a bottom side of a constructional component facing the implant.

29. The tooth implant according to claim 20, further comprising a support sleeve, in which the adapter is held during preparation of an impression and through which the screw that secures the screw-in adapter on the implant remains accessible also after preparation of the impression.

* * * * *